United States Patent [19]

Abramson

[11] Patent Number: 4,508,533
[45] Date of Patent: Apr. 2, 1985

[54] SURGICAL DRAIN

[76] Inventor: Daniel Abramson, 7671 San Mateo Dr., E., Boca Raton, Fla.

[21] Appl. No.: 167,905

[22] Filed: Jul. 14, 1980

[51] Int. Cl.³ ............................................ A61M 27/00
[52] U.S. Cl. ........................................ 604/35; 604/30; 604/39; 604/45; 604/126
[58] Field of Search ................... 128/350 R, DIG. 26, 128/276, 340, 349 R; 604/30, 35, 39, 45, 126, 604/175, 282, 4.3, 101, 180

[56] References Cited

U.S. PATENT DOCUMENTS

| 3,430,631 | 3/1969 | Abramson | 604/282 |
| 3,663,965 | 5/1972 | Lee et al. | 604/175 |
| 3,753,439 | 8/1973 | Brugarolas | 604/43 |
| 3,777,761 | 12/1973 | Sheridan | 604/175 |
| 4,100,246 | 7/1978 | Frisch | 604/101 |
| 4,149,539 | 4/1979 | Cianci | 604/180 |

Primary Examiner—V. Millin
Attorney, Agent, or Firm—Larson and Taylor

[57] ABSTRACT

An improved surgical drain of the Abramson type having a triple lumen catheter with a drainage lumen, an irrigation lumen, and an air ventilation lumen. The improved drain is interfitted with a connector providing a suction port for the drainage lumen, an irrigation port for the irrigation lumen, and an air intake port for the air ventilation lumen. Closure plugs for each port may also be provided. The improved drain further includes a suture means for securing the drain in place and stabilizing it and a softened distal end portion to reduce tissue necrosis upon insertion of the drain into the patient's body.

20 Claims, 5 Drawing Figures

U.S. Patent  Apr. 2, 1985  4,508,533
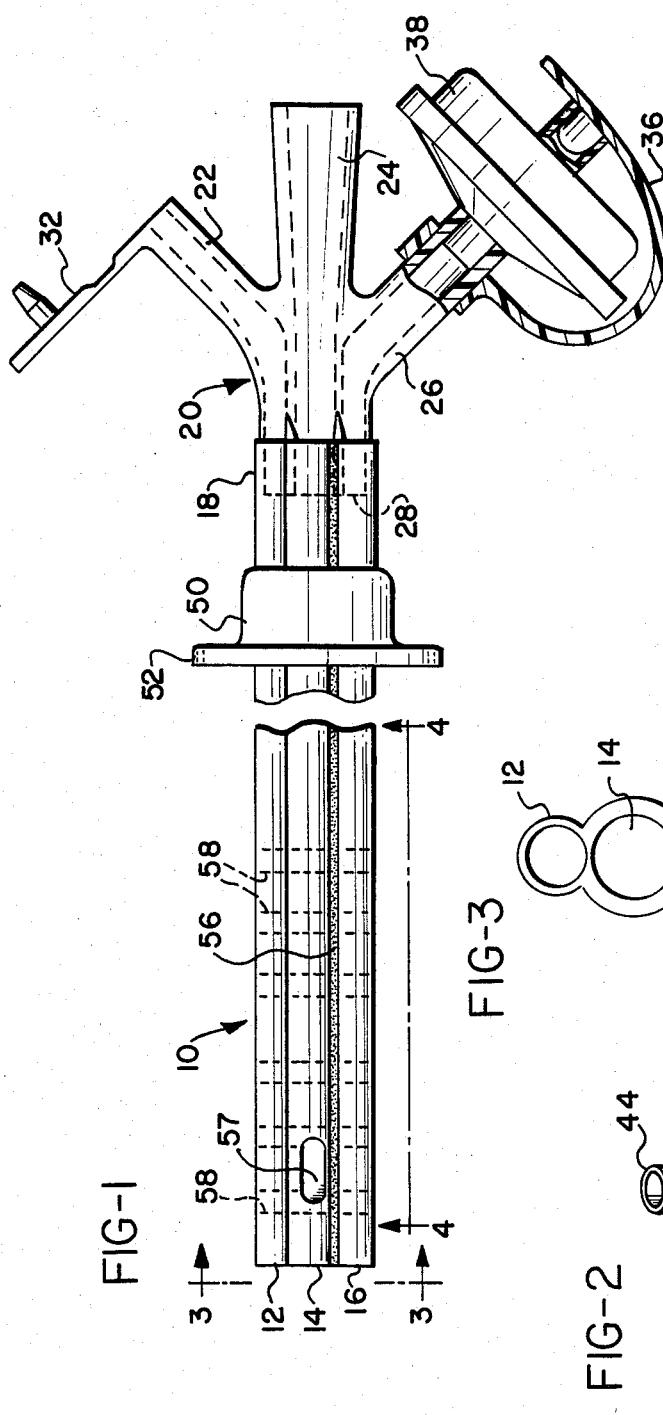

SURGICAL DRAIN

BACKGROUND OF THE INVENTION

The present invention relates to an improved surgical drain, and more particularly, to a surgeon's drain of the Abramson Drain type, but having a cushioned end, a grommet or suture strip, an interfit connector, and other improved features.

In U.S. Pat. No. 3,430,631 there is disclosed a surgeon's drain which has become widely known as the Abramson Drain. In a preferred form, as shown in FIG. 4 of U.S. Pat. No. 3,430,631, a central tube used for drainage has joined to it second and third tubes of substantially the same length. The second and third tubes not only help prevent the collapse of the drainage tube and serve as possible back-up drainage tubes should collapse take place despite this precaution, but one of the second and third tubes can be used to admit air to the area being drained and the other or both can be used as a path in and out for irrigation.

In practice the Abramson Device as disclosed and claimed in U.S. Pat. No. 3,430,631 has taken the form of a triple lumen catheter of extruded polyvinyl chloride. The central drainage lumen is typically connected to a source of suction; whereas, one of the second and third tubes is used for air ventilation and the other used for introduction of irrigation fluid.

While the Abramson Drain of this type has become widely accepted because of its unique features, improvements are still desired. For example, with the commercial Abramson Drain construction, it is necessary for the users to jerry-rig a connection to the suction device if it is to be for sump drainage. Likewise, it is difficult to provide for closed drainage with the present form of the Abramson drain. It would also be desirable to filter any air ventilation since room air contains bacteria which may otherwise contaminate the wound.

Other areas of improvement relate to the need for a means to locate the drain by X-rays should its location need to be determined or to ensure that if any of the drain is accidentally left in the body of the patient, it can be discovered by X-ray. Similarly, it would be desirable to anchor the drain in place, and yet have the ability to pull the drain outwardly in increments as the wound heals and cut off the excess drain outside the body of the patient. Finally, with a firm drain having a blunt tip there is the possibility of pressure necrosis at the time the drain is placed against internal viscera.

Of course, it is known to use multiple port connections for gastrointestinal tubes (see Frisch U.S. Pat. No. 4,100,246) and hemostatic devices (see Cianci U.S. Pat. No. 4,149,539). It is also known to add a radiopaque and suture strip along a drainage tube (Sheridan U.S. Pat. No. 3,777,761); to use a grommet around wires, tubes and conductors for facilitating passage of those wires, tubes and conductors through the skin (Lee U.S. Pat. No. 3,663,965) and to use a soft padded sheath around a drainage device to prevent tissue necrosis (Brugarolas U.S. Pat. No. 3,753,439). However, those techniques are not directly related to Abramson type drain and to my knowledge have not previously been suggested by others for use on an Abramson Drain.

Accordingly, the need exists for an improved Abramson type drain which has all of the capabilities and safety features desirable from the standpoint of ease and adaptability in use as well as being non-hazardous to the patient and effective for drainage from the interior of a wound, or cavity or part being surgically treated.

SUMMARY OF THE INVENTION

The present invention meets that need by providing an improved drain including the following features:

(a) a triple lumen catheter of the Abramson type having a three-tube connector designed to interfit with the three lumens of the drain and adapted to provide a suction port, an irrigation port, and a bacterial filtered air intake port, each port designed to be easily closed if desired;

(b) a grommet or suture strip used as a stabilizing anchor for the drain and/or a means for suturing it to a patient's skin; and (c) a cushioned or softened end or tip to facilitate insertion of the drain into the body cavity and reduce pressure necrosis of surrounding tissue. Other improved features include the use of a radiopaque strip along the length of the drain and forming the catheter body in one piece of a soft extruded silicon rubber.

Thus, an internal catheter is formed with three lumens, in accordance with the earlier Abramson patent. It may be made of a latex, polyvinyl chloride, or other plastic material, but as mentioned silicone rubber is preferred. It is also preferably an integral extrusion molded unit having a central lumen and two side lumens. The central lumen is the primary drainage lumen. A three-tube connector made of a harder plastic material has a corresponding central suction port for attachment through a suction tube to a drainage bottle. The outside ports connect to the side lumens, one or both of which may be used for air ventilation. Other uses for these side lumens include irrigation, aspiration, taking cultures, and installation of medication for treating existing infections or prevention thereof. The side lumens are usable for simple drainage, along with the central lumen, if suction is not applied.

However, as mentioned, a preferred use is for sump drainage. In that case it is desirable to filter the air intake and that port of the connector may be permanently fitted with a bacterial filter, or the filter may be removably attached. In either case the air intake port is also fitted with a plug which may be used to close the lumen when closed suction (no air) is desired or when leakage from that port is to be prevented.

The irrigation port also is fitted with a plug. Actually, the irrigation port is usually closed with the plug except for periods of irrigation; although, it may be left open as a further air inlet as well. Likewise, continuous irrigation can be accomplished by placing a drip attachment through intravenous type tubing connected to a drip bottle.

Although the three-tube connector may be bonded to the catheter or molded directly thereto, preferably, it is friction fit into the proximal end of the triple lumen catheter. In this way it is removable if the drain is to be cut and shortened. The connector may be reinserted following such procedures. It may also be removed from the catheter at anytime when suction is discontinued and overflow drainage or simple drainage may continue to be collected in a normal fashion, i.e., on a sterile dressing or into a bag.

A grommet which fits snuggly, but slidably about the three lumen catheter is the preferred form of suture means. The grommet may be sutured to the skin (although it need not be since it will aid placement and stabilization of the drain even without permanent attachment) as a stabilizing anchor for the drain. This places the drain securely so that it cannot be pulled from the skin and deeper structures. Still because the catheter is slidable through the grommet, it is possible to pull the catheter outwardly in increments as the wound heals and the excess portions may then be cut off to shorten the drain. In that instance, grommet serves the additional functions of preventing the catheter from being lost in the wound if the catheter is cut off too close to the body or if the connections are separated and cut away from the drain.

An alternative suture means is to mold or adhere a suture strip along a lateral edge of the catheter. The suture strip may be a thin filament bonded along the edge, or pieces of filament bonded thereto intermittently along the edge. Likewise, it could be a continuous or intermittent series of protuberances molded onto an edge of the catheter as a part of the extrusion molding process. In any event, the suture strip is to avoid placement of sutures or safety pins in the catheter itself with consequent leakage.

The cushioned or softened end can be formed as simply as by placing a series of holes in the walls of the distal end of each lumen. Those holes tend to weaken the wall strength of the plastic so that it will give or flex more easily at the distal end. They are also important in serving as an interconnection between each of the lumens and the exterior of the catheter so that drainage, irrigation and ventilation can better take place.

An alternative means of reducing tissue necrosis is to make the distal end filamentous or in the form of a porous grid. Again, this will weaken the wall strength of the plastic at the distal end. Finally, a separate softer piece of material could be adhered to the distal end of the catheter, also in an effort to cushion its impact on the internal viscera. In both of these instances, however, it may still be desirable to include a number of inter-lumen connecting holes as well.

When all or any number of these features are added to the Abramson type of drain, an improved surgical drain is formed which offers the promise of even widerspread use and acceptance than the original Abramson Drain.

Accordingly, it is an object of the present invention to provide an improved surgical drain making it easier for connection to suction devices, irrigation means, etc.; having a greater stability in place, and reducing pressure necrosis to the surrounding tissue on insertion of the drain into the body cavity.

Other objects and advantages of the invention will be apparent from the following description, the accompanying drawing and the appended claims.

BRIEF DESCRIPTION OF THE DRAWING

FIG. 1 is a plan view of a preferred embodiment of the improved surgical drain of the present invention.

FIG. 2 shows an alternative connector for the improved surgical drain of the present invention.

FIG. 3 is a cross-sectional view of the triple lumen catheter along lines 3—3 of FIG. 1.

FIG. 4 is a side view of the triple lumen catheter along lines 4—4 of FIG. 1.

FIG. 5 is a plan view of a section of the catheter portion of the drain, and showing an alternative suture means.

DETAILED DESCRIPTION OF THE PREFERRED EMBODIMENTS

Referring to FIG. 1, there is shown a preferred embodiment of the improved surgical drain of the present invention. That drain has a triple lumen catheter 10, with lumens 12, 14, and 16 integrally formed therein and extending parallel along the length of catheter 10. Central lumen 14 is the primary drainage lumen. Side lumens 12 and 16 may serve as the irrigation lumen and air ventilation lumen, respectively.

At the proximal end 18 of catheter 10 is a connector 20. Connector 20 has an irrigation port 22, corresponding to and in fluid connection with irrigation lumen 12; a suction port 24, corresponding to and in fluid connection with drainage lumen 14; and an air intake port 26, corresponding to and in fluid connection with air ventilation lumen 16. As shown connector 20 has an end portion 28 inserted within proximal end 18 of catheter 10. The end portion 28 is sized so that it will tightly fit into the proximal end 18 of catheter 10 to form a friction bond which will resist leakage of fluids. It will not, however, prevent removal of connector 20 from catheter 10 at appropriate times, as explained above. Also as explained above, connector 20 may be in the alternative permanently bonded to catheter 10 by use of an appropriate adhesive or it may be integrally molded as a part of the catheter forming operation.

Irrigation port 22 has a plug 32 attached to it for closure of the irrigation port 22 when irrigation lumen 12 is not in use. Of course, as mentioned, irrigation lumen 12 may be used for purposes other than irrigation, including an additional or backup drainage lumen, an additional air intake, a means for taking cultures, installation of medication, etc. For that purpose port 22 is sized so that a Luer lock syringe or I.V. tubing can be inserted.

Suction port 24 is sized so that it can be easily connected, by use of an adapter, or directly, to drainage tubing (not shown) which connects with a suction device, and empties into a container or bag. When as connected, the drain is designed to be used as a sump drain. In that instance, plug 32 will be used to close irrigation port 22, but air intake port 26 will generally be open as to reduce pressure on the body cells as suction is applied at the distal end of catheter 10, through drainage lumen 14.

Air intake port 26, like irrigation port 22, has a plug attached to it. Plug 36 is used to block air intake port 26 at times when closed suction (no air) is desired. It is also used to close air intake port 26 when that port is otherwise not in use for sump drainage. Also attached to air intake port 26 is a bacterial filter 38. The bacterial filter may be a triple stage filter capable of maximum flow and yet capable of removal of particles down to 0.3 micron size. Such filters of this type are known in the art, but to my knowledge have not previously been used with an Abramson Drain. The bacterial filter 38 helps eliminate air born infection of the wound which is being drained.

An alternate form of connector is shown in FIG. 2. Alternate connector 40, also has an irrigation port 42, a suction port 44, and an air intake port 46. Like connector 20 of FIG. 1, it has an end 48 adapted to be removably fit into proximal end 18 of catheter 10. The difference is that alternative connector 40 does not have closure plugs attached to the irrigation port and air intake port, nor is a bacterial filter formed as an integral part of the air intake part. Rather, separate closure plugs (not shown) can be used with irrigation port 42 and air intake port 46, as well as suction port 44. Likewise, a separate bacterial filter unit (not shown) may be used in either of ports 42 or 46, or both if both are used for air ventilation. Finally, in alternate connector 40, suction port 44 is shown as being ribbed or threaded for ready connection to a standard suction tube arrangement (not shown).

Referring back to FIG. 1 there is a grommet 50 which fits tightly over catheter 10, but is slidable along the length of the catheter 10. Grommet 50 has a circumferential lip 52 which is designed to abut the patients body at the place of entry of the catheter portion of the drain. As such it stabilizes the drain in place. For further stabilization, lip 52 may be sutured to the patient's skin. Since grommet 50 is slidably disposed about the catheter 10, the depth of the catheter placement may be decreased by withdrawing the catheter 10 through grommet 50. If a connector 20 is removable, as preferred, then the excess portions of catheter 10 may be cut off to shorten the drain and connector 20 removed from the cut off portion and reconnected to the remaining portion of catheter 10.

An alternative suture means is shown in FIG. 5 where protuberances 54 are formed intermittently along a lateral wall or walls of the upper portion of catheter 10 (but not at the distal end since they might occlude the drainage holes), in this case along the outside wall of air lumen 16. Protuberances 54 may be molded into catheter 10 as a part of the catheter formation process. Rather than being intermittent, it may be a continuous bead molded therein, or it may even be a separate thin filament (continuous or intermittent) bonded to the lateral wall or walls of catheter 10. Again, the purpose is to provide a suture means which avoids placement of sutures or safety pins in the drain itself.

Finally, FIG. 1 (as well as FIG. 5) shows placement of a radiopaque strip 56 along the length of catheter 10. Formation of such radiopaque strips are common and may take the form of a strip of X-ray opaque filler added to at one point the plastic as the catheter 10 is being extrusion molded during formation. It may also be a painted-on strip of radiopaque material.

FIG. 3 shows a cross-sectional view of catheter 10, with lumens 12, 14, and 16, being the same as in FIGS. 1 and 5. It also shows the relative sizes of those lumens in the preferred embodiments of this invention. Obviously, other sizes may be used. FIG. 3 also illustrates the open end of the catheter so that there is access to the wound from the distal ends of lumens 12, 14 and 16 which are in fluid connection with the devices attached to the drain by connector 20 at the proximal end.

Other means for providing fluid connection to the area to be treated, includes holes 57, as shown in FIG. 1, and holes 58, as shown in FIG. 3. Holes 58 are formed in the outside wall of side lumens 12 and 16 at the distal end of the catheter 10. Similar holes are formed in the walls between central lumen 14 and side lumens 12 and 16. These provide for an interlumen communication at the distal end, as well as an interconnection with the exterior of the catheter. Accordingly, as an example, when drainage occurs, the fluid to be drained will enter not only through the open end of lumen 14 and holes 57, but also through holes 58, into lumens 12 and 16, and by the inter-lumen connection into lumen 14 for exit through suction port 24.

Another function of the holes 57 and 58 is to weaken the wall strength of the plastic at the distal end of catheter 10. This permits easier flexing, bending, and movement of that portion as it is pushed against the body tissues on insertion of the drain into the wound. Other means for providing a softened portion at the distal end includes filamentation of the plastic walls there, forming a porous grid in them, or attachment of a softer piece of material at the distal end. None of these concepts are shown in the drawings, but are readily visualized. Other ways for providing a softened distal end portions may also suggest themselves to one of ordinary skill in the art.

As is apparent, the improved surgical drain of the present invention offers a number of advantages over the Abramson Drain, which is itself quite unique and a leader in its field. Addition of such improvements to the Abramson Drain may increase the costs, which certainly is a factor since such drains are disposable items, but the attendant advantages are believed to more than make up for the cost increase. These advantages, including the ease with which various modes of operation may be achieved using the connector of the preferred or alternate embodiment should be clear.

While the article herein described constitutes a preferred embodiment of the invention, it is to be understood that the invention is not limited to this precise article, and that changes may be made therein without departing from the scope of the invention.

What is claimed is:

1. A surgical drain comprising:
   (a) a triple lumen catheter body having distal and proximal ends,
   (b) a three-tube connector interfit with said triple lumen catheter body at the proximal end and adapted to provide a suction port, an irrigation port, and an air intake port, each of which may be easily closed,
   (c) a suture means as a stabilizing anchor for the drain, and
   (d) a softened portion at the distal end of said catheter body to facilitate insertion of the drain into the body cavity and reduce pressure necrosis of the surrounding tissue.

2. The surgical drain of claim 1 wherein said three-tube connector has attached plugs for at least said irrigation port and said air intake port.

3. The surgical drain of claim 2 wherein said air intake port of said three-tube connector has a bacterial filter attached to it.

4. The surgical drain of claim 1 wherein said three-tube connector is friction fit within said triple lumen catheter body end is removable therefrom.

5. The surgical drain of claim 1 wherein said suture means is a grommet slidably disposed about said catheter body.

6. The surgical drain of claim 1 wherein said suture means is a suture strip or protuberance along the exterior of a portion of said catheter body.

7. The surgical drain of claim 6 wherein said strip or protuberance is located intermittently along said catheter body.

8. The surgical drain of claim 1 wherein said distal end of said catheter body has a series of holes in each of the triple lumens, said holes serving to soften said distal end as well as to interconnect each of the lumens to each other and to the exterior of the catheter for improved drainage and suction.

9. The surgical drain of claim 8 wherein said distal end of said catheter body has a filamentous or porous structure which serves to soften said distal end.

10. The surgical drain of claim 1 wherein said softened portion of the distal end comprises a softer piece attached to said distal end.

11. The surgical drain of claim 1 wherein a radiopaque strip is located along a portion of the length of said catheter body.

12. The surgical drain of claim 1 wherein said catheter body is an integral one of soft extruded silicone rubber.

13. A surgical drain comprising, in combination, a triple lumen catheter body having distal and proximal ends, a connector on the proximal end of the catheter body, a suction port, irrigation port and air intake port in said connector, attached plugs on said connector for closing at least said irrigation port and said air intake port, the distal end of said catheter body being formed with a series of openings in each of the lumens therein, at least the distal end of the catheter body being readily flexed as the catheter body is pushed against body tissues to reduce pressure necrosis of the surrounding tissues.

14. A surgical drain according to claim 13 and further including a suturing means on said catheter body as a stabilizing anchor for the drain.

15. A surgical drain comprising, in combination, a catheter body having three lumens therein, openings in at least one of said lumens in the distal end of the catheter body, a connector on the proximal end of said catheter body, the connector having passageways therein in communication with the lumens in the catheter body, the proximal end of the connector having suction, irrigation and air intake ports, the irrigation and air intake ports being spaced from the suction port, a radiopaque stripe located along a portion of the length of the catheter body, at least the distal end of the catheter body being readily bendable as the catheter body is pushed against body tissues to reduce pressure necrosis of the surrounding tissues.

16. A surgical drain according to claim 15 and further including plugs for at least the irrigation and air intake ports, said plugs being attached to the connector.

17. A surgical drain according to claim 15 and further including a suturing means mounted on said catheter body.

18. A surgical drain according to claim 15 and further including a filter means on said air intake port.

19. A surgical drain according to claim 15 wherein the openings in the lumens in the distal end of the catheter body are in each of said lumens and interconnect the lumens for improved drainage and suction.

20. A sump drain comprising:
   (a) an integral extruded catheter having distal and proximal ends and comprising:
      (i) a first lumen for the drainage of body fluids by suction;
      (ii) a second lumen for the passage of filtered air;
      (iii) a third lumen for the passage of irrigation fluid, said first, second and third lumens extending parallel to each other along the major portion of the longitudinal length of the catheter;
      (iv) a funnel portion at its proximal end, said funnel portion having a connector receiving port extending from the first lumen, a filtered air intake port extending from the second lumen, and an irrigation port extending from the third lumen;
      (v) holes at its distal end, said holes connecting each of the first, second, and third lumens to the exterior of the catheter;
   (b) means for closing the irrigation port;
   (c) a connector, said connector being arranged and constructed so that fluid may pass from the first lumen through the connector, said connector having a proximal end including a suction port;
   (d) means for closing the suction port of the connector;
   (e) a bacteria filter, said bacteria filter having means for filtering bacteria from air and being arranged and constructed so that air may pass through the bacteria filter and into the second lumen, said bacteria filter having a bacteria filter air intake port for the intake of air;
   (f) means for closing the bacteria filter air intake port; and
   (g) a collar slidably disposed about the catheter.

* * * * *